US009341601B2

(12) United States Patent
Sandrin et al.

(10) Patent No.: US 9,341,601 B2
(45) Date of Patent: May 17, 2016

(54) ELASTOGRAPHY DEVICE AND METHOD

(75) Inventors: Laurent Sandrin, L'Hay les Roses (FR); Matteo Bosisio, Paris (FR); Cécile Bastard, Paris (FR)

(73) Assignee: ECHOSENS, Paris (FR)

( * ) Notice: Subject to any disclaimer, the term of this patent is extended or adjusted under 35 U.S.C. 154(b) by 1042 days.

(21) Appl. No.: 13/132,712

(22) PCT Filed: Dec. 2, 2009

(86) PCT No.: PCT/FR2009/052373
§ 371 (c)(1),
(2), (4) Date: Aug. 3, 2011

(87) PCT Pub. No.: WO2010/063951
PCT Pub. Date: Jun. 10, 2010

(65) Prior Publication Data
US 2011/0301468 A1    Dec. 8, 2011

(30) Foreign Application Priority Data

Dec. 4, 2008 (FR) ...................................... 08 58278

(51) Int. Cl.
*A61B 8/14* (2006.01)
*G01N 29/22* (2006.01)
*A61B 5/00* (2006.01)
*A61B 8/00* (2006.01)
*A61B 8/08* (2006.01)
*G01N 29/04* (2006.01)

(52) U.S. Cl.
CPC ............ *G01N 29/223* (2013.01); *A61B 5/0051* (2013.01); *A61B 5/6843* (2013.01); *A61B 8/00* (2013.01); *A61B 8/485* (2013.01); *G01N 29/043* (2013.01); *A61B 8/543* (2013.01)

(58) Field of Classification Search
None
See application file for complete search history.

(56) References Cited

U.S. PATENT DOCUMENTS

| 6,066,096 A * | 5/2000 | Smith et al. .................... 600/439 |
| 6,085,749 A * | 7/2000 | Wardle et al. .................. 128/845 |
| 6,425,865 B1 * | 7/2002 | Salcudean et al. ............ 600/437 |
| 2002/0068870 A1 * | 6/2002 | Alam et al. .................. 600/446 |
| 2003/0105398 A1 * | 6/2003 | Vitek ............................. 600/437 |
| 2004/0111026 A1 * | 6/2004 | Schoenfeld ................... 600/437 |

(Continued)

FOREIGN PATENT DOCUMENTS

| FR | 2 843 290 | 2/2004 |
| FR | 2 869 521 | 11/2004 |
| WO | WO 2008/038184 | 4/2008 |

OTHER PUBLICATIONS

Sandrin et al. Transient elastography: a new noninvasive method for assessment of hepatic fibrosis. Ultrasound in Med & Biol, Vo. 29, No. 12, pp. 1705-1713, 2003.*

(Continued)

*Primary Examiner* — Long V Le
*Assistant Examiner* — Bradley Impink
(74) *Attorney, Agent, or Firm* — Pillsbury Winthrop Shaw Pittman LLP

(57) ABSTRACT

An elastography device for quantitatively and/or qualitatively measuring the viscoelastic properties of any medium, includes a deformable tube for positioning the ultrasonic transducer located at the end of the deformable tube and for holding it so as to ensure, during at least one measurement, perpendicularity and contact between the ultrasonic transducer and the medium.

19 Claims, 2 Drawing Sheets

(56) References Cited

U.S. PATENT DOCUMENTS

| | | | |
|---|---|---|---|
| 2005/0107663 A1* | 5/2005 | Saadat et al. | 600/104 |
| 2005/0203398 A1* | 9/2005 | Sandrin et al. | 600/438 |
| 2005/0267368 A1* | 12/2005 | Boctor et al. | 600/443 |
| 2006/0016006 A1* | 1/2006 | Whitmore et al. | 5/601 |
| 2007/0080275 A1 | 4/2007 | Stachowski et al. | |
| 2011/0006767 A1* | 1/2011 | Sack et al. | 324/309 |
| 2011/0028797 A1* | 2/2011 | Yee et al. | 600/231 |

OTHER PUBLICATIONS

International Search Report as issued for PCT/FR2009/052373.

Bastard et al.; "Assessment of the elastic properties of heterogeneous tissues using transient elastography: Application to the liver"; Ultrasonics Symposium, 2008., IUS 2008., IEEE, IEEE, Piscataway, NJ, USA, Nov. 2, 2008, pp. 317-320.

* cited by examiner

ELASTOGRAPHY DEVICE AND METHOD

CROSS REFERENCE TO RELATED APPLICATIONS

This application is the U.S. National Stage of PCT/FR2009/052373, filed Dec. 2, 2009, which in turn claims priority to French Patent application No. 0858278, filed Dec. 4, 2008, the entire Contents of all applications are incorporated herein by reference in their entireties.

The present invention relates to a device and a method for measuring the viscoelastic properties of any medium.

The present invention more particularly relates to a device and a method for quantitatively and/or qualitatively measuring the viscoelastic properties; such as the elasticity and/or the viscosity of a human or animal biological tissue. More specifically, such a device and such a method are suitable for measuring the viscoelastic properties of biological tissues belonging to laboratory animals or from tissue sample.

In order to measure the tissue viscoelastic properties, it is known to use the pulsed elastography, as described, for example, in patent application number FR 2843290.

This document presents an implementation of a device 10 according to the prior art (FIG. 1). This device 10 comprises a probe 1 equipped with a vibration generator 2 generating a low-frequency elastic wave in a tissue, for example by vibration, and analyzing the propagation of this low-frequency elastic wave by means of high-frequency ultrasonic waves emitted and received by an ultrasonic transducer 4 during the propagation of the low-frequency elastic wave.

In addition, it should be noted that the user 6 positions said probe 1 manually to ensure permanent contact between the tissue and the ultrasonic transducer 4. Said probe 1, having the vibration generator 2 and the ultrasonic transducer 4, also includes a trigger 5 for controlling them. The whole is connected to a computer 9.

Such a device is suitable for measuring the viscoelastic properties of large-size organs, for example the human liver, located in the vicinity of the epidermis against which the probe 1 is positioned.

Yet, such a device has drawbacks. In particular, it is not suitable for small-sized organs. In fact, the probe generates a tissue compression when affixed or even positioned in the vicinity or in contact with the organ (the smaller the volume of the tissue is, the higher the compression phenomenon is).

In addition, such a device is not suitable for small organs because the size of the ultrasonic transducer is very significant and the probe is approximately and randomly positioned.

An example of this is the mouse, whose epidermis surface allowing access to the liver is about 1 cm². This dimensional limitation does not allow the user to ensure an optimal positioning which depends not only on the size of the tissue but also on the differences between individuals and/or between species.

An additional drawback is that the user has to manually hold, on the one hand, a constant and satisfactory contact between the ultrasonic transducer and the epidermis so that the ultrasounds are capable of propagating and, on the other hand, an optimal perpendicularity.

Yet, to trigger low-frequency elastic waves, the user presses the trigger 5 which brings about variations in terms of contact between the probe and the epidermis, distorting thus the perpendicularity and, de facto, leading to an overestimation of measurements close to the ultrasonic transducer.

In addition, such a movement raises problems of repeatability of the measurements. Indeed, once the position of the ultrasonic transducer has been modified, it is impossible to position again the ultrasonic transducer at exactly the same location where the first measurements have been made. This is very detrimental for measurements that are carried out on heterogeneous tissues, such as, for example, the kidney.

Furthermore, an overestimation of the measured elasticity, due, inter alia, to a diffraction phenomenon in the field close to the low-frequency wave generation source, occurs over a thickness which depends, in particular, on the dimensions of this source, on the viscoelastic properties, on the medium, on the thickness of the fat layer, as well as on the low-frequency elastic wave.

This thickness, below which measurements are not possible, is about 20 mm for a center frequency f of the low-frequency elastic wave of 50 Hz. To remedy this problem, data on this thickness are disregarded, namely 20 mm, in the calculation of the viscoelastic properties, thereby prohibiting measurements on a thickness less than 20 mm.

In this context, the aim of the invention is to provide a non-invasive device making it possible to overcome the above problems by proposing a device whereby it is possible to precisely hold and position, perpendicularly to and in contact with the tissue, an ultrasonic transducer so as to determine the viscoelastic properties thereof.

Such a device is also advantageous thanks to its design, and though it requires further knowledge and numerous developments, offers an easy to use and noninvasive device of which cost is low.

To this end, the invention provides an elastography device for quantitatively and/or qualitatively measuring the viscoelastic properties of any medium, said device comprising;
 a vibration generator for generating at least one low-frequency elastic wave;
 an ultrasonic transducer for observing the propagation of said at least one low-frequency elatic wave;
 a trigger for triggering at least one measurement;
 said at least one measurement comprising the following steps of:
 generating at least one low-frequency elastic wave in a medium;
 emitting and acquiring simultaneously to the generation of at least one low-frequency elastic wave high-frequency ultrasounds using said ultrasonic transducer to observe the propagation of said at least one low-frequency elastic wave;
 said device being characterized in that it comprises a deformable tube, positioned between said vibration generator and said ultrasonic transducer, for holding said ultrasonic transducer located at the end of said deformable tube and for holding it so as to ensure, during at least one measurement, perpendicularity and contact between said ultrasonic transducer and the medium.

What is meant by deformable tube is a tube freely movable in several directions, with no angular limitation, and which holds its position in the absence of any stress applied to move it.

The medium is interchangeably referred to as tissue.

Besides the main characteristics which have been mentioned in the previous paragraph, the device according to the invention may have one or more additional characteristics listed below, whether considered individually or in all technically possible combinations:
 said elastography device includes a support spatially hold the ultrasonic transducer;
 said elastography device includes a spring system located between said ultrasonic transducer and said deformable tube;

said device includes at least one rod capable of transmitting the low-frequency elastic waves from said vibration generator to said ultrasonic transducer;

said device includes a gripping tube;

said vibration generator is formed by a vibrating table;

said vibration generator is formed by a loudspeaker-type secondary device;

said elastography device includes a fine-tuning system for rotationally and/or translationally adjust the position of said ultrasonic transducer;

said vibration generator is located at the end of said deformable tube where the ultrasonic transducer is located;

said vibration generator is located at the opposite end of the deformable tube where the ultrasonic transducer is located;

said device includes a high-frequency imaging ultrasonic array;

said device is coupled with an organic synchronization device;

said ultrasound transducer has an active diameter smaller than 3 mm.

The present invention also relates to an elastography method for quantitatively and/or qualitatively measuring the viscoelastic properties of any medium characterized in that it implements a device according to the invention; said method comprises at least the following steps of:

positioning said at least one ultrasonic transducer, by deforming said deformable tube, perpendicularly and in contact with the medium;

translationally and/or rotationally adjusting the position of said ultrasound transducer;

triggering at least one measurement;

holding said ultrasonic transducer in position and in contact during at least one measurement;

said measurement comprising the following steps of:

generating at least one low-frequency elastic wave;

emitting and acquiring simultaneously to the generation of at least one low-frequency elastic wave high-frequency ultrasounds using said ultrasonic transducer to observe the propagation of said at least one low-frequency elastic wave;

calculating at least one parameter relating to the viscoelastic properties of the medium such as the displacement variations and/or the deformations and/or the displacement speeds and/or the deformation speeds caused in the medium or more generally any parameter relating to the viscoelastic properties;

calculating the viscoelastic properties of the medium;

An additional advantageous feature is that said ultrasonic transducer is held in position and in contact with the medium during a series of measurements, by said deformable tube.

Advantageously, the low-frequency elastic waves are randomly triggered by the user starting in a synchronized manner with a breathing and/or heart rate.

Preferably, the high-frequency ultrasonic emission is performed over a frequency range comprised between 8 MHz and 100 MHz, and preferably between 10 MHz and 50 MHz.

Similarly, the low-frequency elastic waves are generated over a frequency range between 50 Hz and 10000 Hz, said low-frequency elastic waves may be of about 400 Hz.

In addition, said at least one low-frequency elastic wave is generated by mechanical vibration and/or by mechanical compression and/or by ultrasonic focalization.

These and other features and advantages of the present invention will become more apparent from the following description of different embodiments of the invention, illustrated only by way of non-limitative example in the accompanying drawings, in which.

Figure 3:
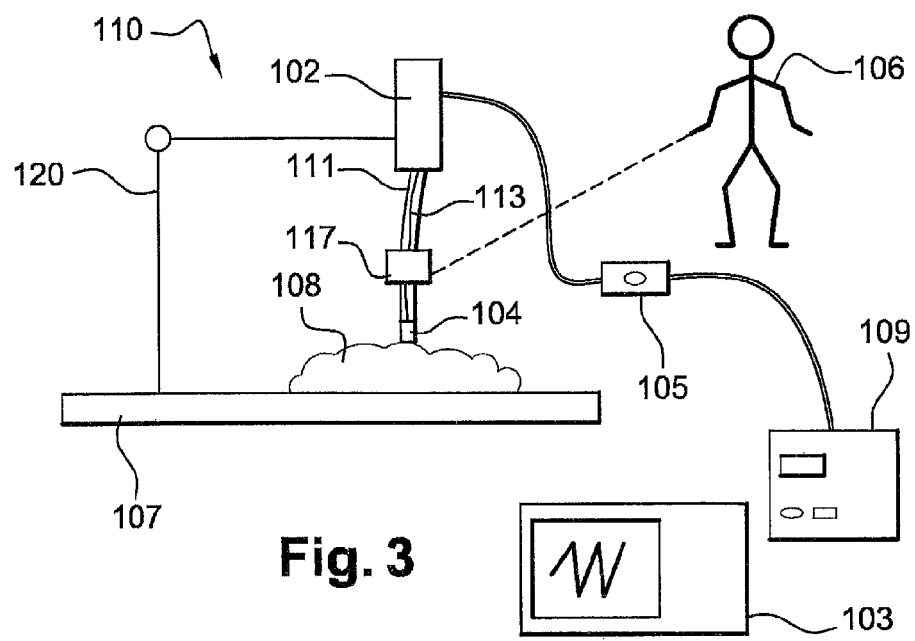
Figure 4:
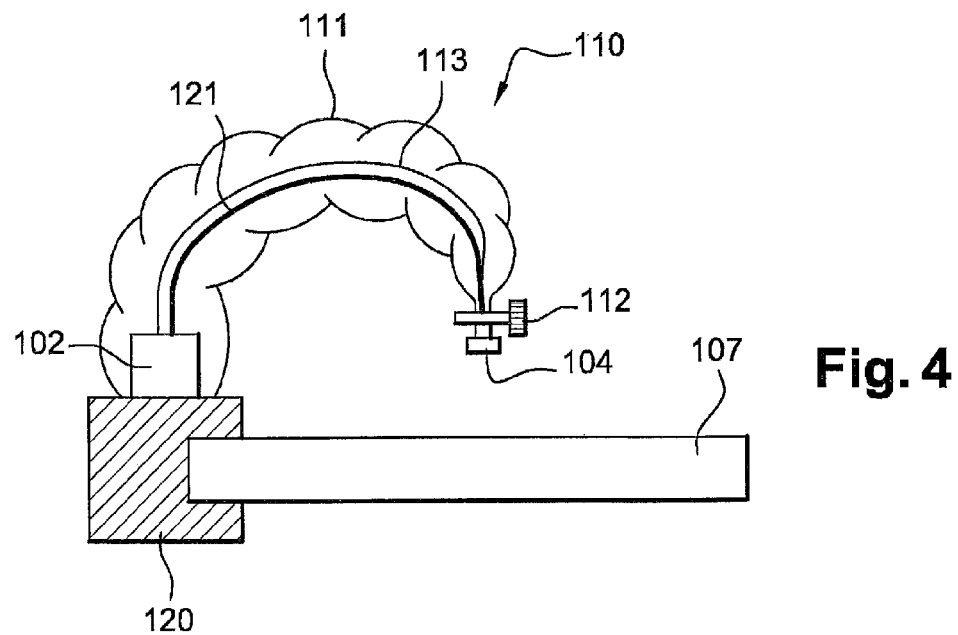
Figure 5:
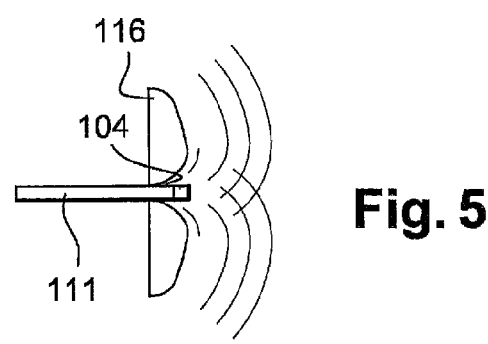

FIG. 3. is a simplified schematic representation of device according to the invention equipped with a gripping tube FIG. 4. is a simplified schematic representation of a device according to the invention equipped with a vise-like support FIG. 5 is a simplified schematic representation of an ultrasonic array for imaging that may be part of the elastography device For reasons of clarity, the same elements have been designated by similar references. Similarly, only the elements useful for understanding the invention have been illustrated schematically the scale not being taken into consideration.

For the remainder of the description, what is meant by elastography is a technique for measuring the viscoelastic properties wherein a vibration generator generates, by direct or indirect contact with a tissue, one or more low-frequency elastic waves propagating in this tissue.

The temporal shape of such a low-frequency elastic wave may be arbitrary, but more generally of pulsed type, transient or periodic (continuous monochromatic).

This vibration is generally obtained in a mechanical manner but may also be obtained by radiation pressure, by ultrasonic hyperthermia or by internal vibrations of the body (heartbeat, pulse, etc. . . . )

In addition, different types of one membered or multi membered ultrasonic transducers may be used. It can for example be, in a non limitative way, a ring-type, annular, 2D matrix, linear or convex array transducer, a one membered, three-membered, star-type transducer, etc. . . .

In addition, laboratory animals refer particularly, in a non-limitative way, to amphibians, fish, reptiles and mammals, such as mice, rats, rabbits, cats, dogs and monkeys.

Figure 1:
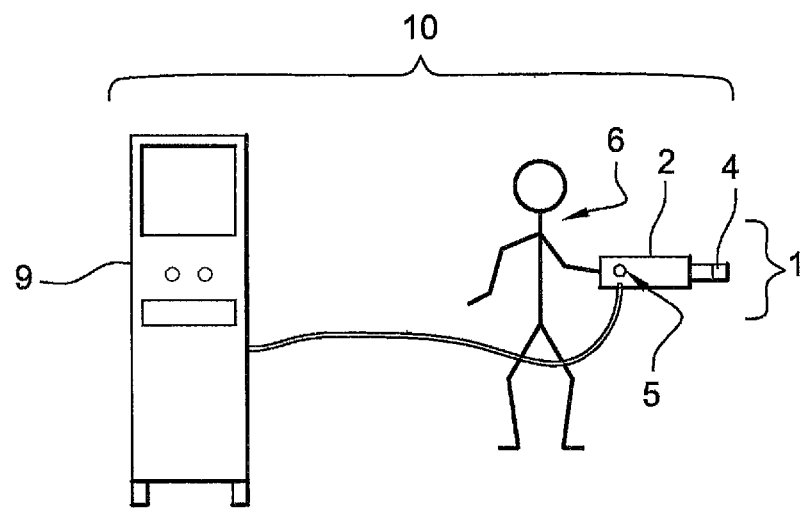
FIG. 1 is a simplified schematic representation of a device 10 according to the prior art.

FIG. 1 shows the prior art devices.

Figure 2:
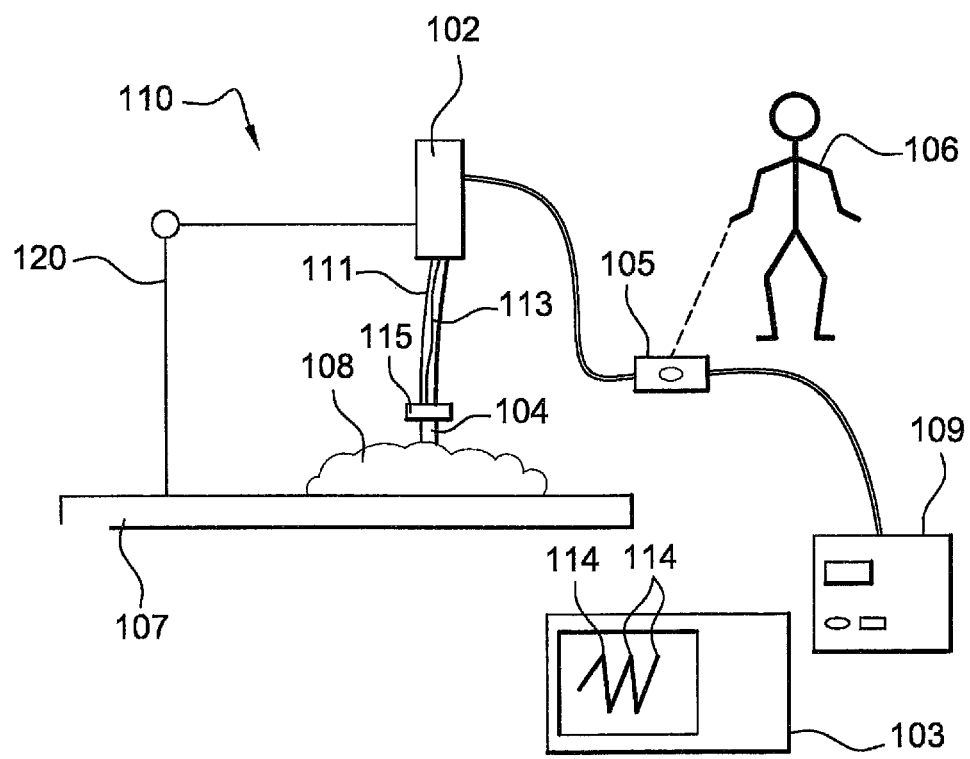
FIG. 2 is a simplified schematic representation of a device according to the invention for ensuring the positioning of at least one ultrasonic transducer.

In FIG. 2 are shown a user 106; an organic synchronization device 103, a table 107, a laboratory animal 108 and an elastography device 110 according to the invention, the device 110 according to the invention comprises:

a deformable tube 111;

at least one ultrasonic transducer 104;

a support 120;

a vibration generator 102;

a trigger 105;

a coaxial wire 113 for the transmission and the reception of ultrasonic signals;

a spring system 115;

an analysis, processing and computation system 109.

The deformable tube 111 ensures the positioning and the holding of at least one ultrasonic transducer 104 and ensures the transmitting of low-frequency elastic waves. More particularly, this tube 111 holds its position when it is deformed The support 120 ensures the holding:

of the deformable tube 111 of the vibration generator 102 for generating low-frequency elastic waves;

of at least one ultrasonic transducer 104 for the ultrasonic emission and acquisition The support 120 makes it possible to hold the above mentioned components without requiring any intervention from the user 106.

The trigger 105 makes it possible to trigger measurements.

The spring system 115 located, for example, between the end of the deformable tube 111 and the ultrasonic transducer 104 makes it possible to compensate the stress exerted on the tissue upon contact between the ultrasonic transducer 104 and said tissue. Thus, no compressive stress is generated on the tissue. This makes it possible to avoid any modification of the viscoelastic properties of the tissue.

In the following, the operation of the device 110 will be described according to the invention.

The first step is to position the ultrasonic transducer 104 in contact with the tissue to be measured or in contact with the tissue surrounding said tissue.

To this end, the user 106 deforms the deformable tube 111 which is held by the support 120 so as to bring the ultrasonic transducer 104 as close as possible to the tissue.

This deformable tube 111 is advantageous thanks to its structure which allows, on the one hand, to easily move the ultrasonic transducer 104 in space without any angular limitation, and on the other hand, to hold the desired position without deforming the deformable tube 111 thanks to its ductility.

Thus, the deformable tube 111 makes it possible to adjust the position of the ultrasonic transducer 104 so as to respect the perpendicularity and the contact of said ultrasonic transducer 104 with the tissue to be measured.

The structure of the deformable tube 111 may be formed by:
- multiple elements connected by a ball joint; in other words, the deformable tube 111 in this case is formed by an articulated tube;
- an elastically deformable tube, or
- more generally, any other type of tube which can:
  - retain its shape when no stress is applied; and
  - change its shape when a stress is applied.

Moreover, according to a possibility provided by the invention, the device is coupled to a surgical navigation system, not illustrated, of:
- first, locating the area of interest to be measured using a medical imaging device, of x-ray magnetic resonance imaging type or of any other imaging type enabling the sight of the biological tissues;
- then, positioning the ultrasonic transducer 104 in an electro-mechanic, electro-hydraulic, electro-pneumatic or in a manual way.

Therefore, such a positioning enables the user 106 to perform measurements of viscoelastic properties.

Said measures consisting in:
- generating at least one low-frequency elastic wave using the vibration generator 102;
- emitting and acquiring simultaneously to the generation of at least one low-frequency elastic wave high-frequency ultrasounds using said ultrasonic transducer 104 to observe the propagation of said at least one low-frequency elastic wave.

To this end, the ultrasonic transducer 104 should, during the measurements:
- stay in contact with the tissue so as not to lose the ultrasonic signal and to make at least one series of measurements at the same location. This is ensured by the specific structure of the deformable tube 111 allowing it to retain its shape.
- be positioned perpendicularly to avoid an overestimation of the measurements. This feature being achieved by the deformable structure, free of any angular limitation, of the deformable tube 111.

Specifically, small organs or organs whose accessibility is reduced require such a positioning precision.

This difficulty of access is frequently encountered in small laboratory animals such as mice, for instance, the adult wild mice usually 8 cm long has a liver with a volume of about 1.5 $cm^3$, yet, much of it is located behind the ribcage, hence forcing the user 106 to carry out measurements over a skin area between 10 $mm^2$ and 1 $cm^2$ and more specifically, on a depth generally between 1 mm and 20 mm below the dermis and preferably 2 to 6 mm.

To this end, during the generation of at least one low-frequency elastic wave, the vibration generator 102 transmits the vibration to the ultrasonic transducer 104 via the flexible tube 111. As shown in FIGS. 2, 3 and 4, the vibration generator 102 is separated from the ultrasonic transducer 104 by the deformable tube 111. The ultrasonic transducer 104 has au active diameter less than or equal to 3 mm, This small diameter allows, firstly, to position the ultrasonic transducer 104 on a small area and, secondly, to avoid the diffraction zone encountered by the prior art devices.

In addition, measurements over a depth of less than 20 mm require the generation of low-frequency elastic waves having centre frequency between 50 and 10000 Hz and preferably, between 100 and 3000 Hz, this frequency may be typically of about 400 Hz.

Then, to observe the propagation of the low-frequency elastic waves, the ultrasonic transducer 104 of the one membered or multi-membered type adapted for generating high-frequency ultrasounds for example ranging between 8 and 100 MHz and preferably, between 10 and 50 MHz.

Such measurements are triggered by the user 106 via the trigger 105, said trigger is connected to the vibration generator 102 and to the ultrasonic transducer 104 by a wire, by a computer network of WIFI type or by any other device allowing the transfer of data.

Thus, the vibration generator 102 generates at least one low-frequency elastic wave, which can be transmitted by the ultrasonic transducer 104 itself or by a non-illustrated secondary device, such as, for example, a loudspeaker.

In addition, it should be noted that the cardiac and the respiratory rates naturally generate low-frequency elastic waves of the monochromatic type. Therefore, there are three types of low-frequency elastic waves in the tissue interfering with each other, typically these waves can be generated by:
- the device according to the invention
- the cardiac system
- the respiratory system The devices according to the prior art ignore interferences generated by the respiratory and/or cardiac rate. However, these biological phenomena generate movements of the reference frame highly altering the measurement of the viscoelastic properties or making it even impossible.

During inhalation, air enters the lungs, which increase in size, and then, inversely, the lungs volume decreases during exhalation. This phenomenon of inflation and deflation can lead to large displacements and thus distort measurements.

Thus, an elastography device according to the prior art restricts the field of use. This measurement inability is considerable in small animals, because unlike humans, whose respiratory rate is low, namely 16 pulses per minute, the respiratory rate of laboratory animals is very high. More specifically, while the rabbit is at almost 60 pulses per minute, the mouse is at about 220 pulses per minute.

Advantageously, the device 110 according to the invention offers the possibility to synchronize the generation of low-frequency elastic waves with the biological frequency using an electrocardiogram and/or a pulmonary synchronizer 103 more commonly known as organic synchronization.

Indeed, the respiratory cycle is composed alternately of an inspiration during which the air enters the lungs then inversely of an expiration during which air is expelled from said lungs causing strong tissue displacements and tissue extensions and compressions.

Therefore, it is important to initiate measurements repeatedly at a determined time so as each obtained measurement or series of measurements is representative of a similar area of interest.

To this end, the device of the invention can be coupled to an organic synchronizing device 103 making it possible to synchronize the measurements with the respiratory rhythm.

This implementation is necessary and advantageous in mice whose liver has 6 lobes (middle lobe, left lobe, 2 right lobes and 2 caudal lobes), which liver may have not only an organic heterogeneity but also a tissue heterogeneity requiring the user 106 to perform the measurements at a precise location for at least a series of measurements.

With reference to FIG. 2 the user 106 may for instance trigger a series of measurements synchronized with an organic synchronization system 103 adapted to trigger low-frequency elastic waves to each peak 114 representative of the maximum wave front corresponding to a maximum inhalation.

Thus, the measurements are triggered by the user but only start when the peak 114, representative of the maximum wave front, is reached.

Then, to observe the propagation of these low-frequency elastic waves, high-frequency ultrasonic waves are emitted and acquired simultaneously by the ultrasonic transducer 104.

These high-frequency ultrasonic waves generally range between 8 and 100 MHz and preferably between 10 and 50 MHz.

These data are then transmitted to a data processing, computation and analysis system 109, informing the user 106 of the viscoelastic properties of the area of interest in real time.

According to an embodiment of the invention shown in FIG. 3, the elastography device 110 is provided with a gripping tube 117.

Thus, the low-frequency excitation generated by the vibration generator 102 is transmitted to the ultrasonic transducer 104 via the deformable tube 111 located inside the gripping tube 117.

Such an implementation is advantageous thanks to its workability, since the user 106 manually positions the ultrasonic transducer 104 without altering the transmission of the low-frequency elastic waves performed by the deformable tube 111, from the vibration generator 102, to the ultrasonic transducer 104. The later, in addition to its ultrasonic emission and acquiring function, serves as a probe.

Furthermore, the support 120 can be of the vise type as illustrated in FIG. 4.

The minimum size of this support facilitates the handling and the transport of the elastography device.

As shown in FIG. 4, the elastography device may include a fine-tuning system 112, to rotationally and/or translationally adjust the position of the ultrasonic transducer 104 without deforming the deformable tube 111.

According to an alternative provided by the invention shown in FIG. 4 the low-frequency elastic waves are transmitted to the probe 104 via a rod 121 located within the deformable tube 111.

In addition, according to an additional alternative of a device 110 according to the invention shown schematically in FIG. 5, the device 110 is provided with an echograph type ultrasonic imaging array 116, allowing the user to ensure that the ultrasonic transducer 104 is positioned in the axis of the area of interest.

To this end, the device of the invention may comprise at least one ultrasonic imaging array 116 and at least one elastography-specific ultrasonic transducer 104.

The ultrasonic transducer 104 moves in a direction perpendicular or substantially perpendicular to the imaging array plan so as to transmit at least one low-frequency elastic wave from the vibration generator 102 in the medium. According to a non-illustrated alternative the ultrasonic transducer can be moved along x, y, and/or z axis and/or in rotation.

The high-frequency echographic array 116, informs the user about the spatial location and the movement of organs, allowing it therefore to position the probe 104 in the axis of said organ of interest. Thus, the ultrasonic transducer 104 located at the end of the deformable tube 111 and in contact with the epidermis is used to observe the propagation of low-frequency ultrasonic waves indicative of the viscoelastic properties of the biological tissue.

In addition, as shown in FIG. 5, the high-frequency ultrasonic array 116 has a specific shape the purpose of which is to cover an optimal area. For this purpose, said shape may be curved, circular, oval, rectangular, triangular or be any other geometric shape leading to the same result, namely the coverage of an area by high-frequency ultrasounds.

The possible steps for implementing a device according to the invention illustrated in FIG. 5 include:
  imaging the tissue with a high-frequency ultrasonic imaging array 116 to determine the spatial location of the area of interest;
  positioning the ultrasonic transducer 104 in the axis of the area of interest using the deformable tube 111
  generating at least one low-frequency elastic wave;
  simultaneously emitting and acquiring high-frequency ultrasounds using the elastography transducer 104 to measure the viscoelastic properties.

According to an advantageous non-illustrated alternative of the invention, said high-frequency ultrasonic array 116 is composed of multiple elements, said elements can be used, on the one hand, to image the environment, and, on the other hand, to generate at least one low-frequency elastic wave.

The array may generate at least one low-frequency elastic wave in the medium in a way which is:
  mechanical, by displacing at least one element;
  mechanical, by displacing said array
  electronic, by ultrasonic focalization.

According to an additional alternative provided by the invention, the vibration generator may be formed by the table 107 on which the tissue to be measured seats. In such an implementation, the user 106 shakes the table 107 then follows the movement of the ultrasonic waves generated by said table 107 via ultrasonic transmission and acquisition of the ultrasonic transducer 104.

It should be noted that the application field of the invention relates to laboratory animals. Such an application may of course be extended to the pharmaceutical, food, chemical, or to the medical fields to determine the viscoelastic properties of human or animal tissue samples or cell samples from in vivo, ex-vivo, in vitro cell cultures.

The invention is described above by way of example. It is understood that a man skilled in the art is capable of producing different alternatives of the device and of the method for measuring the elasticity of a human or animal tissue, particularly with regard to the disposition or arrangement of the various elements composing said device or the order as well as the importance of the steps of said method without departing from the scope of the patent.

The invention claimed is:

1. An elastography device for quantitatively and/or qualitatively measuring the viscoelastic properties of any medium, said device comprising:
   a vibration generator configured to generate at least one low-frequency elastic wave;
   an ultrasonic transducer configured to observe a propagation of said at least one low-frequency elastic wave;
   a trigger configured to trigger at least one measurement, said at least one measurement being performed by
      generating the at least one low-frequency elastic wave in a medium, and
      emitting and acquiring simultaneously to the generation of the at least one low-frequency elastic wave high-frequency ultrasounds using said ultrasonic transducer to observe the propagation of said at least one low-frequency elastic wave;
   a deformable tube positioned between said vibration generator and said ultrasonic transducer, the deformable tube being freely movable to spatially move without angular limitation the ultrasonic transducer and having a ductility that allows the deformable tube to hold the ultrasonic transducer in position after movement of the deformable tube, wherein the deformable tube is configured to hold said ultrasonic transducer located at the end of said deformable tube so as to ensure, during at least one measurement, perpendicularity and contact between said ultrasonic transducer and the medium, and
   a support attached to the vibration generator and configured to spatially hold the ultrasonic transducer.

2. The device according to claim 1, comprising a spring system located between said ultrasonic transducer and said deformable tube.

3. The device according to claim 1, comprising at least one rod capable of transmitting the low-frequency elastic waves from said vibration generator to said ultrasonic transducer.

4. The device according to claim 1, comprising a gripping tube.

5. The device according to claim 1, wherein said vibration generator is formed by a vibrating table.

6. The device according to claim 1, wherein said vibration generator is formed by a loudspeaker-type secondary device.

7. The devices according to claim 1, wherein said device includes a fine-tuning system configured to rotationally and/or translationally adjust the position of said ultrasonic transducer.

8. The device according to claim 1, wherein said vibration generator is located at the end of said deformable tube where the ultrasonic transducer is located.

9. The device according to claim 1, wherein said vibration generator is located at the opposite end of the deformable tube where the ultrasonic transducer is located so that said vibration generator is directly connected to said opposite end of the deformable tube.

10. The device according to claim 1, wherein said device includes at least one high-frequency ultrasonic imaging array.

11. The device according to claim 1, wherein said device is coupled to an organic synchronization device.

12. The device according to claim 1, wherein said ultrasonic transducer has an active diameter of less than 3 mm.

13. An elastography method for quantitatively and/or qualitatively measuring the viscoelastic properties of any medium, said method comprising:
   providing the elastography device of claim 1;
   positioning said at least one ultrasonic transducer, by deforming said deformable tube, perpendicularly and in contact with the medium;
   translationally and/or rotationally adjusting the position of said ultrasound transducer;
   triggering at least one measurement;
   holding said ultrasonic transducer in position and in contact during the at least one measurement; said at least one measurement comprising:
   generating at least one low-frequency elastic wave;
   emitting and acquiring simultaneously to the generation of the at least one low-frequency elastic wave high-frequency ultrasounds using said ultrasonic transducer to observe the propagation of said at least one low-frequency elastic wave;
   calculating at least one parameter relating to viscoelastic properties of the medium such as the displacement variations and/or the deformations and/or the displacement speeds and/or the deformation speeds caused in the medium or more generally any parameter relating to the viscoelastic properties; and calculating the viscoelastic properties of the medium.

14. The method according to claim 13, wherein said ultrasonic transducer is held in position and in contact with the medium during a series of measures, by said deformable tube.

15. The method according to claim 13, wherein said low-frequency elastic waves are randomly triggered by the user starting in a synchronized manner with a breathing and/or heart rate.

16. The method according to claim 13, wherein said high-frequency ultrasonic transmission is performed over a frequency range comprised between 8 MHz and 100 MHz.

17. The method according to claim 13, wherein said low-frequency elastic waves are generated over a frequency range comprised between 50 MHz and 10000 MHz.

18. The method according to claim 13, wherein said low-frequency elastic waves are of about 400 Hz.

19. The method according to claim 13, wherein said at least one low-frequency elastic wave is generated by mechanic vibration, and/or by mechanic compression and/or by ultrasonic focalization.

* * * * *